United States Patent [19]
Brewer

[11] Patent Number: 5,173,273
[45] Date of Patent: * Dec. 22, 1992

[54] CASSETTE FOR DENTAL INSTRUMENTS

[76] Inventor: Charles A. Brewer, 105 Via Wazier, Newport Beach, Calif. 92660

[*] Notice: The portion of the term of this patent subsequent to Sep. 25, 2007 has been disclaimed.

[21] Appl. No.: 595,971

[22] Filed: Oct. 11, 1990

[51] Int. Cl.$^5$ .......................... A61B 19/02; B65D 1/34; B65D 6/04; B65D 41/18
[52] U.S. Cl. .................................... 422/300; 422/297; 422/310; 206/439; 206/63.5; 206/562; 206/564; 220/324; 220/306
[58] Field of Search ............... 422/297, 299, 300, 310; 206/63.5, 439, 562, 564; 220/323, 324, 306

[56] References Cited

U.S. PATENT DOCUMENTS

| | | | |
|---|---|---|---|
| 4,153,178 | 5/1979 | Weavers | 220/306 |
| 4,541,992 | 9/1985 | Jerge et al. | 422/300 |
| 4,643,303 | 2/1987 | Arp et al. | 422/300 |
| 4,752,453 | 6/1988 | Nichols | 422/300 |
| 4,959,199 | 9/1990 | Brewer | 422/297 |
| 4,974,140 | 12/1990 | Niles et al. | 220/324 |

FOREIGN PATENT DOCUMENTS

| | | | |
|---|---|---|---|
| 1269052 | 5/1990 | Canada | 220/324 |

Primary Examiner—Robert J. Warden
Assistant Examiner—Theresa A. Trembley
Attorney, Agent, or Firm—Gordon L. Peterson

[57] ABSTRACT

A cassette for dental instruments includes a tray having bottom and a plurality of walls extending to a particular plane, the walls defining first and second generally opposing slots. A lid having a generally planar configuration is adapted to mount on the tray with its outer surface disposed in the particular plane. A fixed tab on the lid is adapted to register with the first slot, while a moveable tab on the lid is slidable between a retracted position and an extended position wherein the moveable tab registers with the second slot.

20 Claims, 3 Drawing Sheets

CASSETTE FOR DENTAL INSTRUMENTS

BACKGROUND OF THE INVENTION

1. Field of the Invention

This invention relates generally to sterilizing trays and more specifically to cassettes adapted to support individually, operating instruments, such as dental instruments, in a sterilizing process.

2. Description of the Prior Art

In a process for sterilizing operating instruments, such as dental instruments, trays have typically been provided to individually support and retain the instruments in a separated configuration. This facilitates ease of handling and disposition within a sterilizing medium such as steam or ethylene oxide. The trays have commonly been provided with lids which are not only removably fixed to the tray but also function to lock each of the instruments in its respective supports. Both the trays and the lids have been provided with an open grate configuration to provide easy access for the sterilizing medium to contact the instruments. The trays and lids have commonly been formed from materials, such as polyethersulfone, which are stable in the presence of the sterilizing medium.

Of particular interest to the present invention is the means by which the lids have been removably fixed to the trays. End walls of the trays have extended from a bottom upwardly to a lip or handle which has extended generally horizontally in a top plane of the tray. Central portions of each end wall and the handle have been vertically slit to form a center support at each end of the tray. The purpose of the vertical slits has been to weaken the center supports so that they can be bent out of the plane of the sidewalls. Slots have been formed in the center supports and positioned to register with tabs on the ends of the lid.

The tabs have been fixed with respect to the lid and positioned to register with the slots when the center supports are in their normal position. Only by bending these center supports out of their normal position has it been possible to lock and unlock the lids with respect to the trays.

Unfortunately the weakening of the end walls, which is necessary to provide the center supports with bendable characteristics, has also made these supports susceptible to breaking. Attempts have been made to stiffen the supports so that they can be less breakable, but this has only resulted in making it more difficult to lock and unlock the lids with respect to the trays. What is required is a simple locking mechanism which can be operable with little force without weakening the walls of the tray.

SUMMARY OF THE INVENTION

These deficiencies of the past are overcome with the present invention which provides for end walls which are not weakened by vertical slits. In fact, the upper lip or handle of the end walls can be unbroken around the entire perimeter of the tray. With this configuration, slots can be formed in relatively rigid end walls of the tray.

In preferred embodiments, the lid is provided with a fixed tab and a movable tab, and is molded with longitudinal and transverse elements which form a grate. A slide is mounted between adjacent grate elements and slidable in opposite directions along those grate elements. The moveable tab is carried by the slide and extends generally in the direction of movement of the slide. The slide is then moveable between extreme positions such as a first position wherein the tab is retracted from the perimeter of the lid and a second position wherein the tab extends beyond the perimeter of the lid. This configuration permits the lid to be easily placed upon the tray with its fixed tab mounted in one of the slots and the slide disposed in its first position with the moveable tab retracted. Then the slide can be advanced to its second position wherein the moveable tab extends to register with the other slot in the adjacent end wall of the tray.

The lid is generally planar in configuration and has a top surface and a bottom surface. When operatively disposed, the top surface of the lid forms a generally planar surface with the upper lip or handle of the tray end walls. The tab is preferably disposed to move beneath the bottom surface of the lid so that the tab does not interfere with the structural integrity of either the lid or the tray handles.

In accordance with the locking mechanism of the present invention, the slide can be easily moved between the first and second positions to lock and unlock the lid from the tray. The end walls of the tray are not weakened and therefore cannot be easily broken. In order to simplify manufacture of the lid, the slide mechanism can be configured to easily snap into its slidable position between adjacent resilient longitudinal grate elements of the lid.

These and other features and advantages of the present invention will be more apparent with a description of preferred embodiments and reference to the associated drawings.

BRIEF DESCRIPTION OF THE DRAWINGS

FIG. 4 is a cross-sectional view taken along lines 4-4 of FIG. 2 and illustrating the region of the locking mechanism;

DESCRIPTION OF PREFERRED EMBODIMENTS

Figure 1:
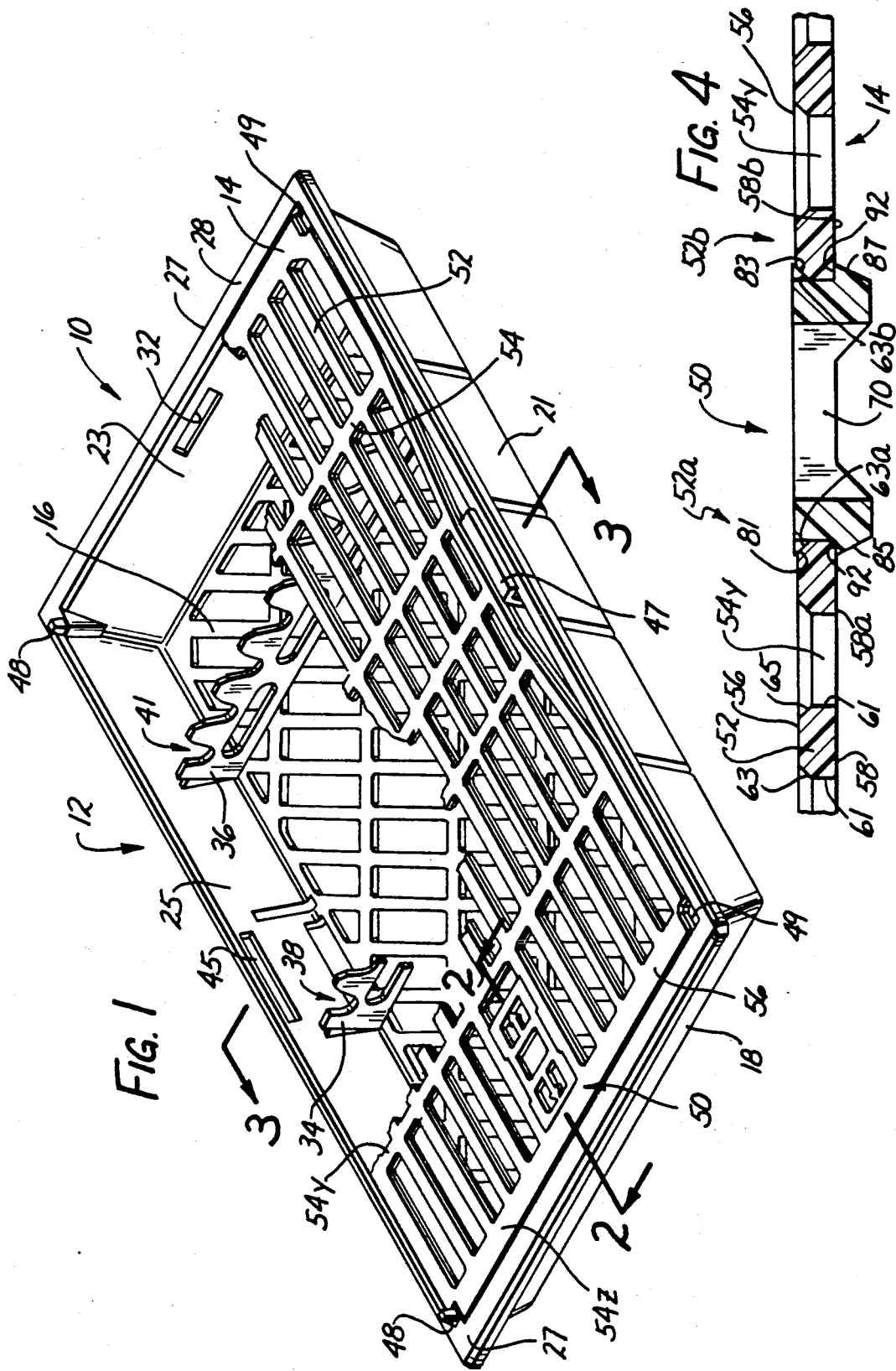
FIG. 1 is a perspective view of one embodiment of the cassette showing a tray and lid associated with this invention.

A cassette for dental instruments is illustrated schematically in FIG. 1 and designated generally by the reference numeral 10. The cassette 10 includes a tray 12 and a lid 14 which is illustrated partially in section in order to show the interior regions of the tray 12. The cassette 10 is adapted to receive a plurality of dental instruments (not shown) which are generally longitudinal in configuration. In this particular embodiment the cassette 10 is provided with a rectangular configuration to receive the dental instruments in a generally parallel relationship and longitudinally with respect to the tray 12.

The tray 12 includes an open grate bottom 16 and a peripheral wall which comprises a plurality of walls 18, 21, 23 and 25 which extend upwardly and transversely to the bottom 16. In this case, the walls 21 and 25 form the longer sidewalls of the rectangular tray 12 while the walls 18 and 23 form shorter end walls of the rectangular tray 12. At the upper extremity, the walls 18, 21, 23, and 25 terminate in a lip 27 which extends around the perimeter of the tray 12 in a generally horizontal orientation substantially parallel to the bottom 16. Along the end walls 18 and 23 the lip 27 protrudes slightly so that in these regions the lip 27 actually forms a pair of handles to support the cassette 10. In the illustrated embodiment, the uppermost surface of the lip 27 defines a plane 28 which is of particular interest to the present invention.

Portions of each of the end walls 23 and 27 define respective apertures or slots 30 and 32. Only the slot 32 is illustrated in FIG. 4; the slot 30 is more apparent with reference to FIG. 2. In this embodiment, the slots 30 and 32 are positioned centrally of their respective end walls 18 and 23. The slots 30 and 32 are generally rectangular in shape and extend longitudinally generally parallel to the bottom 16 and lip 27. It will be apparent that the slots 30, 32 can be otherwise positioned and configured, but it is important that at least one slot be provided in each of the end walls 18 and 23.

Within the tray 12, the sidewalls 21 and 25 can be apertured to receive a pair of upstanding instrument supports 34 and 36. These supports can be similar in shape and configured to form a plurality of notch pairs, one in each of the supports 34, 36 such as the pair of notches designated generally by the reference numerals 38 and 41. Thus the supports 34 and 36 extend generally between the sidewalls 21 and 25, and the respective notch pairs, such as the pair formed by the notches 38 and 41, are adapted to receive one of the dental instruments (not shown). Although more than one of the supports 34, 36 is generally required, the illustrated embodiment is adapted to receive as many as four such supports.

Figure 3:
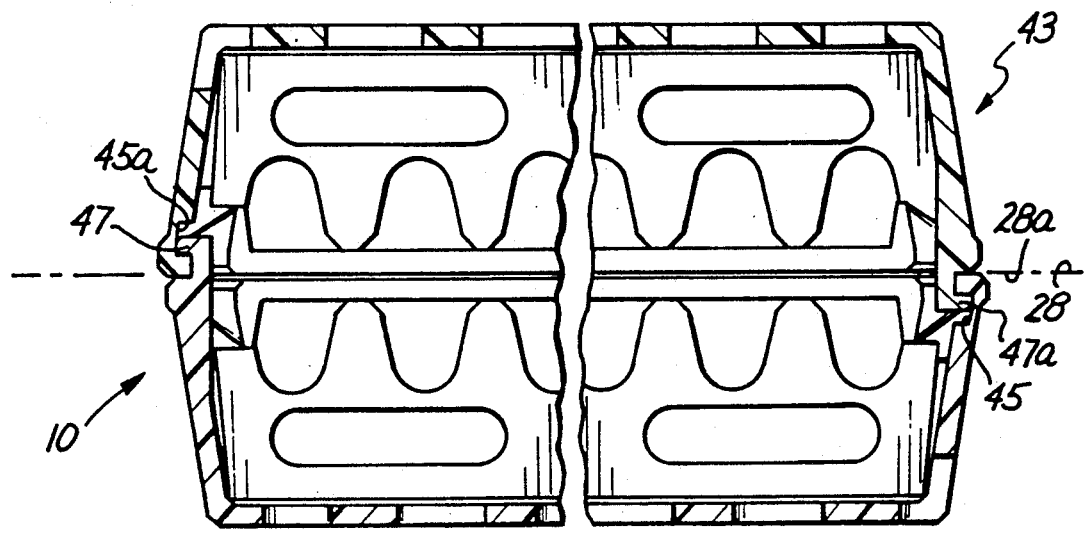
FIG. 3 is a cross-sectional view taken along lines 3-3 of FIG. 1 and illustrating a pair of cassettes mounted lid-to-lid in order to facilitate the sterilizing process.

The cassette 10 is also configured to register with a similar cassette such as that shown generally at 43 in FIG. 3. Thus, the sidewall 25 can be shaped to define a recess 45, generally below the plane 28, while the sidewall 21 is configured to form a latch 47 which extends generally above the plane 28. Referring again to FIG. 3, the inverted tray 43 could include a recess 45a disposed beneath its top plane 28 and a latch 47a disposed to extend above its top plane 28a. Then, with the cassette 43 inverted, its recess 45a registers with the latch 47 of cassette 10 and its latch 47a registers with the recess 45 of the cassette 10.

By thus providing this means for joining a pair of the cassettes, such as the pair including cassettes 10 and 43, the sterilization process is greatly facilitated. A pair of cassettes is easier to handle as it presents a size which is easier to grip. Joining the cassettes in pairs also facilitates stacking the cassettes in a sterilization unit. It is particularly advantageous that the cassettes are joined lid-to-lid; this provides a secondary locking system to retain the instruments in their respective cassettes.

The alignment of cassettes into pairs can be facilitated by providing a plurality of posts 48 (FIG. 1) which are attached to the tray 12 and extend above the plane 28. Complimentary apertures 49 can be formed in either the tray 12 or the lid 14 to receive the associated posts 48 when the cassettes 10 and 43 are suitably aligned for attachment. This alignment of cassettes is also facilitated by forming the trays 12 and lids 14 to present a generally planar top surface. In the illustrated embodiment, only the latch 47 and posts 48 extend above the plane 28.

The present invention is concerned primarily with a locking mechanism for removably attaching the lid 14 to the tray 12. This mechanism is designated generally by the reference numeral 50.

In some embodiments the mechanism 50 will benefit from a particular configuration of the lid 14. For example, in the illustrated embodiment, the lid 14 includes longitudinal rails or bars 52 and transverse rails or bars 54 which are disposed in the configuration of a grate. The longitudinal bars 52 are generally parallel to each other as well as to the sidewalls 21, 25 and the lip 27. With the tray 12 having a generally rectangular configuration, it follows that the longitudinal bars 52 of the lid 14 are generally perpendicular to the end walls 18, 23 and the lip 27 associated with those end walls.

The longitudinal and transverse bars 52 and 54, respectively, are shown in greater detail in FIG. 4. These bars 52, 54 form a top surface 56 of the lid 14. When the lid 14 is operatively disposed on the tray 12 this top surface 56 of the lid is preferably disposed in the plane 28 associated with the lip 27 of the tray 12.

Each of the bars 52 and 54 is also defined by a bottom surface 58 and a pair of side surfaces 61. These side surfaces 61 extend to the bottom surface 58 but are separated from the top surface 56 by a pair of angled surfaces which form shoulders 63 and 65. The angled surfaces of the shoulders 63, 65 extend from the respective side surfaces 61 inwardly and upwardly to the top surface 56. In a preferred embodiment, the shoulders 63, 65 are disposed at an angle such as 45 degrees to the surfaces 56, 58 and 61. Thus the angled shoulders 63, 65 face upwardly and outwardly from their respective bars 52, 54.

An adjacent pair of the longitudinal bars 52 are thus configured in the illustrated embodiment and form a pair of longitudinal supports for the locking mechanism 50. These supports are designated generally in FIG. 4 by the reference numerals 52a and 52b. Various elements of these supports 52a and 52b which are similar to those previously discussed are designated with the same reference numerals followed by the respective lower case letters "a" or "b", For example, the support 52a is defined by an angled shoulder 63a which faces upwardly and generally in the direction an angled shoulder 63b associated with the support 52b.

Figure 5:
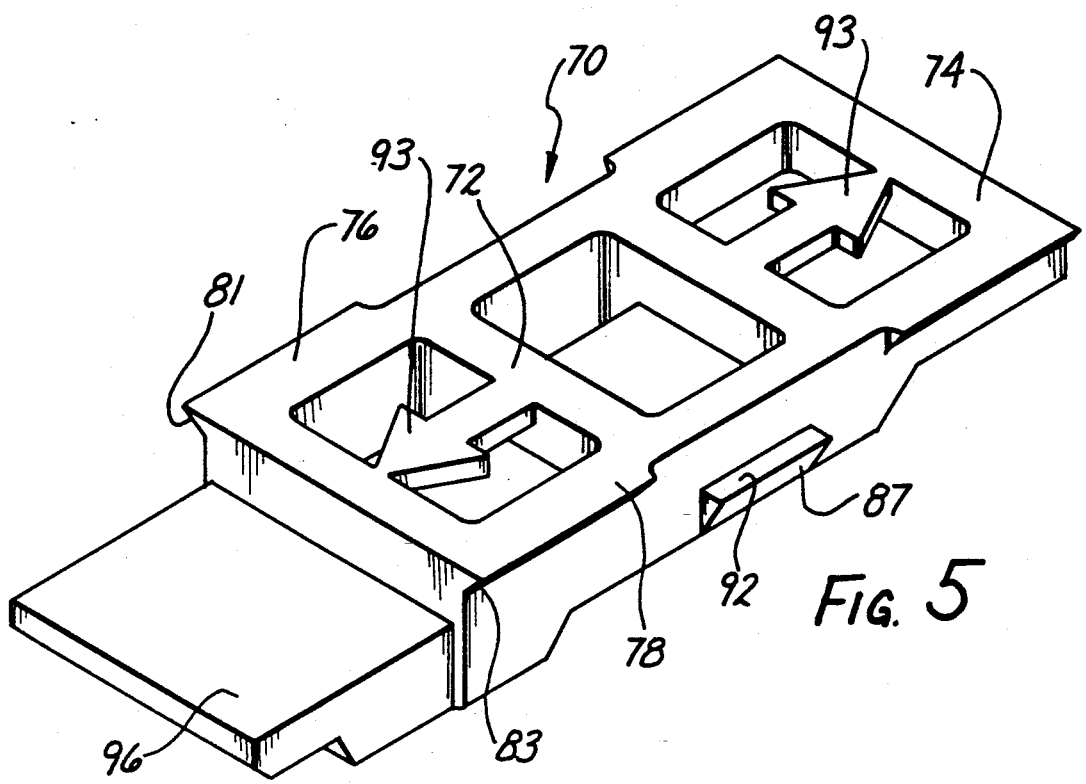
FIG. 5 is an perspective top view of the locking mechanism associated with the present invention.
Figure 6:
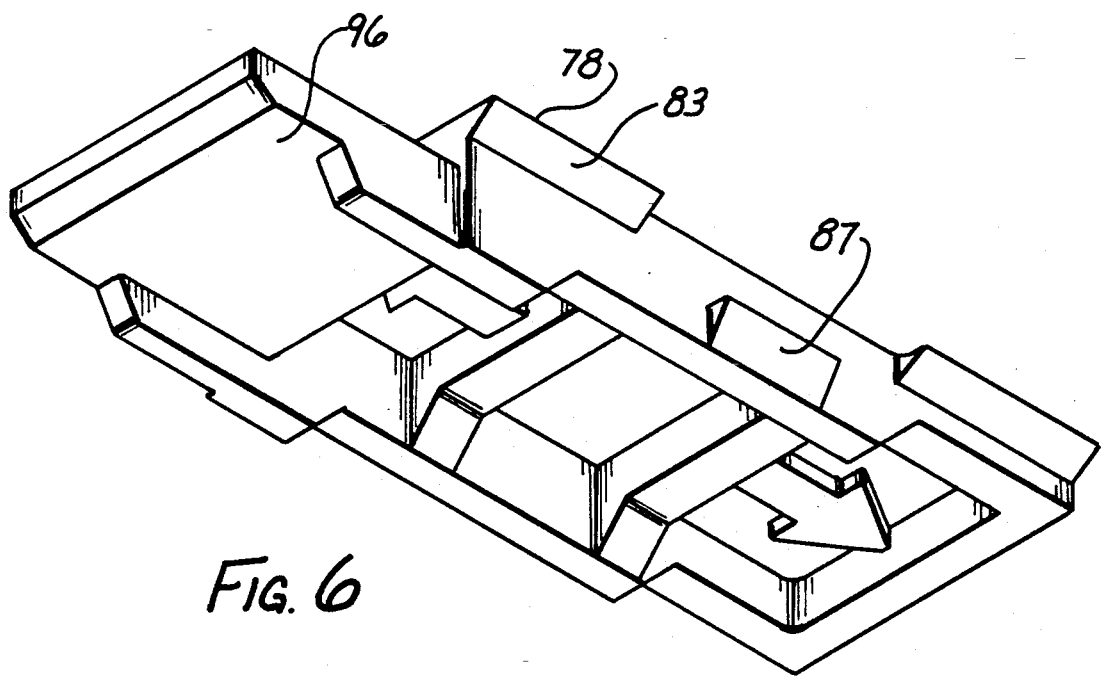
FIG. 6 is an perspective bottom view of the locking mechanism associated with the present invention.

Also included in the locking mechanism 50 is a slide 70 shown in cross-section in FIG. 4 and schematically in FIGS. 5 and 6. The slide 70 is configured to extend between the supports 52a, 52b and positioned to slide longitudinally along these supports between a pair of the transverse bars 54y and 54z. In a preferred embodiment, the transverse bars 54y and 54z form the last two bars at one end of the lid 14.

The slide 70 includes a body member 72 which is generally rectangular in configuration and has a width generally equal to the distance separating the supports 52a and 52b. The length of the body member 72 is generally shorter than the distance separating the transverse elements 54y and 54z. The body member 72 has an upper surface 74 which is preferably in the plane 28 when the slide 70 is operatively disposed. This is desirable in order that the cassette 10 may have a generally flat upper surface.

Extending from the body member 72 in proximity to the surface 74 is a pair of opposing flanges 76 and 78 best illustrated in FIG. 5 and 6. These flanges 76, 78 extend at least partially along the top longitudinal edges of the body member 72. Each of the flanges 76, 78 has a surface 81, 83 respectively, which faces outwardly from the body member 72 and downwardly from the top surface 74. These surfaces 81 and 83 are configured to register with and slide along the respective shoulders 63a and 63b associated with the supports 52a and 52b.

Similarly attached to the body member 72 are a pair of opposing flanges 85 and 87 which are disposed generally lower than the flanges 76, 78. Both of the flanges 85 and 87 have an upwardly facing surface 90, 92 respectively, which can be generally parallel to the surface 74.

The flanges on each side of the body member 72, such as the flanges 78 and 87 are preferably separated by a distance such that the surface 74 and the surface 92 are separated generally by a distance equal to the thickness of the support members 52a, 52b. This of course is equal to the distance between the top surface 56 and the bottom surface 58 of the bars 52, 54. More generally, it is important that the surfaces of the respective flanges 85, 87 be configured to register with and slide along the respective bottom surfaces 58a and 58b associated with the supports 52a and 52b.

Figure 2:
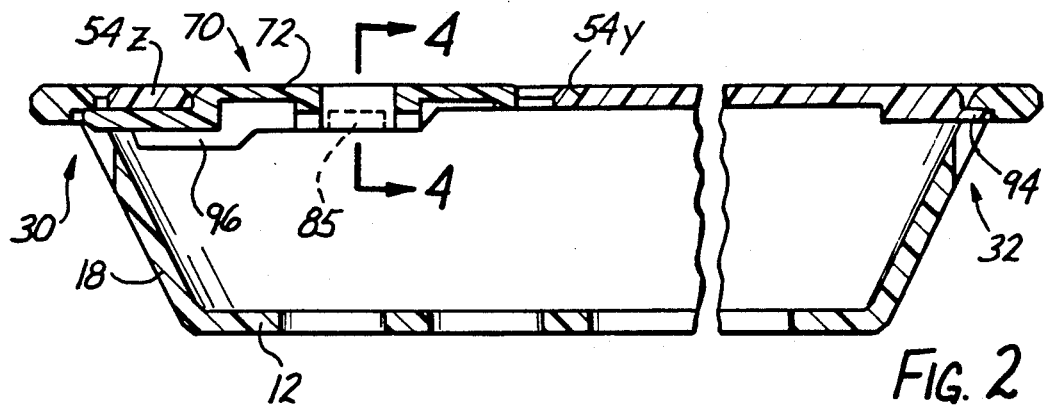
FIG. 2 is a cross-sectional view taken along lines 2-2 of FIG. 1 and showing the locking tab extended to lock the lid to the tray.

In a preferred embodiment, the flanges 85 and 87 are disposed centrally along the longitudinal side of the body member 72. This facilitates mounting the slide 70 between the supports 52a and 52b. As the slide 70 is pressed downwardly between the supports 52a and 52b the centrally located flanges 85 and 87 tend to resiliently separate the supports 52a, 52b between their ends and thereby permit the slide 70 to snap into its operative position as illustrated in FIG. 4. Thus positioned the slide 70 is movable along the supports 52a and 52b between a first position wherein the body member 72 contacts the transverse bar 54y (FIG. 2a) and a second position wherein the body member 72 contacts the transverse bar 54z (FIG. 2).

Indicia can be molded into the body member 72 in the form of arrows 93 which show the direction of movement of the slide 70 between these first and second positions.

It can now be appreciated that it is particularly advantageous that the angled shoulders 63a, 63b be defined beneath the top surface 56 of the supports 52a and 52b. This permits the shoulders 63a and 63b to register with the surfaces 81 and 83, respectively, so that the top surface of the body member 72 can be disposed generally in the plane 28 associated with the tray 12.

The lid 14 is provided with a pair of opposing tabs 94 and 96. The tab 94 is fixed to the lid 14 and is adapted to register with the slot 32 in the end wall 23. The tab 96 is not fixed to the tray 12 but rather is mounted on the slide 70 and extends generally longitudinally from one end of the slide 70. When the slide 70 is moved into its second position, in contact with the transverse bar 54z in FIG. 2, the tab 96 extends along the bottom surface of the lid at the element 54z, the slide also extends beyond the element 54z, that is beyond the edge of the lid 12. Operatively disposed, the tab 96 in this extended position is configured and adapted to register with a slot 30 in the end wall 18.

Figure 2A:
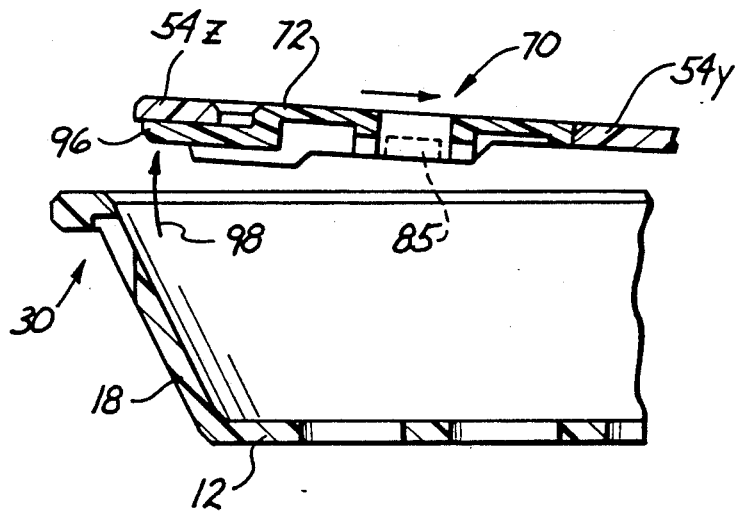
FIG. 2A is a cross-sectional view similar to FIG. 2 wherein the locking tab is retracted and the lid and tray are illustrated in an unlocked relationship.

When the slide 70 is moved to its first position, contacting the transverse element 54y in FIG. 2a, the tab 96 is moved to a retracted position. In this retracted position, the tab 96 does not extend beyond the ultimate element 54z or the edge of the lid 12. In the retracted position, the tab 96 is removed from the slot 30 thereby permitting the lid 12 to be raised for example in the direction of arrow 98 in FIG. 2a.

In operation, the tray 12 would first be loaded with the instruments (not shown) and the lid 14 would be placed over the tray 12 with the slide 70 snapped into its operative position on the lid 14. The fixed tab 94 on the lid 14 would initially be placed into the slot 32 at one end of the tray 12. By moving slide 70 to its first position the tab 96 would be withdrawn to its retracted position thereby permitting the opposite end of the lid 14 to be lowered onto the tray 12. Then by merely moving the slide 70 from its first position to its second position, the tab 96 will be urged into its extended position registering with the slot 30 in the tray 12. This is all that is required to lock the lid 14 to the tray 12 as the tabs 94 and 96 register with their respective slots 32 and 30. A pair of the cassettes, such as the cassette 10 and the cassette 43 can then be joined to facilitate sterilization.

When sterilization has been completed, the cassettes 10 and 43 can be removed and separated. With very little force, the slide 70 can be moved from its second position to its first position. This will withdraw the tab 96 from its extended position in registration with the slot 30 to its retracted position. The lid can then be raised and removed to gain access to the sterilized instruments.

It will be apparent to those skilled in the art that this concept of a locking mechanism for sterilization trays can be configured in embodiments other than those illustrated and described. The supports 52a and 52b as well as the flanges 76, 78, 85, 87 can be provided with any configuration suitable to provide a sliding relationship between the slide 70 and the lid 14. The number, configuration, and location of the slots 30 and 32 may also vary with a particular design. More than one of the slides 70 can be provided although it is preferred that all of the movable tabs, such as the tab 96, be provided at one end of the lid 14 and all of the fixed tabs, such as the tab 94 be provided at the opposite end of the lid 14.

Thus it will be apparent to those skilled in the art that the concept can be otherwise embodied so that the scope of the invention should be ascertained only with reference to the following claims.

I claim:

1. A cassette for dental instruments comprising:
a tray having a bottom and a plurality of walls each extending from the bottom to a particular plane;
means extending between the walls of the tray for individually supporting dental instruments;
portions of the walls defining first and second generally opposing slots;
a lid having a generally planar configuration and an outer surface, the lid being constructed to mount on the tray with the outer surface disposed in the particular plane of the tray;
a first tab disposed in fixed relationship with the lid and adapted to register with one of the slots in the tray; and
a second tab carried by the lid and movable between an extended position and a retracted position, the second tab in the extended position being disposed to register with the second slot to lock the lid to the tray.

2. The cassette recited in claim 1 further comprising:

a slide attached to the second tab and slidable generally in the plane of the lid to move the second tab between the extended position and the retracted position.

3. The cassette recited in claim 2 further comprising indicia on the slide which indicates the possible directions of movement of the second tab.

4. The cassette recited in claim 1 wherein:
the slide has a generally planar configuration and an outer surface; and
the outer surface of the slide and the outer surface of the lid being disposed generally in the particular plane of the tray when the lid is operatively mounted on the tray.

5. The cassette recited in claim 1 wherein the first and second generally opposing slots are generally parallel to the bottom of the tray and to the lid.

6. The cassette recited in claim 1 wherein:
the lid has first and second generally opposed edges;
the first tab extends beyond the first edge of the lid; and
the second tab in the extended position extends beyond the second edge of the lid.

7. A cassette for storing dental instruments comprising:
a tray being constructed to receive dental instruments, the tray having a bottom wall and a pair of generally opposed end walls each extending from the bottom to a particular plane;
portions of the generally opposed end walls defining first and second generally opposed slots;
a lid having first and second major surfaces and being constructed to mount on the tray with the first major surface disposed generally in the particular plane of the tray;
a first tab disposed in fixed relationship with the lid and adapted to register with the first slot in the tray; and
a second tab carried by the lid and slidable along the second major surface of the lid between an extended position and a retracted position, the second tab in the extended position being disposed to register with the second slot to lock the lid to the tray.

8. The cassette recited in claim 7 wherein:
each of the generally opposed end walls has a generally planar configuration and extends in an inclined relationship with the bottom of the tray to an edge which is disposed in the particular plane of the tray.

9. The cassette recited in claim 8 wherein:
the generally opposed end walls portions include a first end wall and a second end wall;
portions of the first end wall define the first slot to extend longitudinally generally parallel to the edge of the first end wall; and
portions of the second end wall define the second slot to extend longitudinally generally parallel to the edge of the second end wall.

10. The cassette recited in claim 9 wherein the first slot is generally parallel to the second slot.

11. The cassette recited in claim 9 wherein each of the end walls is disposed to extend outwardly with progressive positions from the bottom of the tray.

12. The cassette for dental instruments comprising:
a tray having a bottom wall, a peripheral wall extending from the bottom wall and an open top;
means in the tray for supporting dental instruments;
portions of the peripheral wall having first and second apertures opening into the tray;
a lid being constructed to mount on the tray to cover the open top;
a first tab on the lid and adapted to be received in the first aperture in the peripheral wall;
a locking mechanism carried by the lid and movable between a locking position in which the locking mechanism is at least partly receivable in the second aperture to lock the lid to the tray and a releasing position in which the locking mechanism is out of the second aperture to allow the lid to be moved to uncover the open top of the tray; and
at least one of said tray and lid having a plurality of openings therein.

13. The cassette recited in claim 12 wherein the lid includes first and second rails spaced apart by a gap, and means on at least one of the locking mechanism and the first and second rails for mounting the locking mechanism for sliding movement along the first and second rails between the being position and the releasing position.

14. The cassette recited in claim 13 including means for allowing the locking mechanism to be snap fit between the first and second rails.

15. The cassette recited in claim 14 wherein the allowing means includes at least one of said first and second rails being resilient and inclined surfaces on at least one of said one rail and said locking mechanism.

16. The cassette recited in claim 13 wherein the lid has top and bottom surfaces and includes a transverse rail defining an edge of the lid, said locking mechanism includes a tab that extends along the bottom surface of the lid at said transverse rail and is receivable in the second slot in the locking position.

17. The cassette recited in claim 16 wherein the top surface of the lid is essentially planar.

18. The cassette recited in claim 12 wherein the lid includes a plurality of rails spaced apart to define the plurality of openings in the lid and means on the locking mechanism and first and second of the rails for mounting the locking mechanism for movement along the first and second rails between the extended and retracted positions.

19. The cassette recited in claim 12 wherein said first and second apertures are generally opposed.

20. The cassette recite din claim 12 wherein the lid is generally planar and the locking mechanism is movable generally in the plane of the lid.

* * * * *

UNITED STATES PATENT AND TRADEMARK OFFICE
CERTIFICATE OF CORRECTION

PATENT NO. : 5,173,273

DATED : December 22, 1992

INVENTOR(S) : Charles A. Brewer

It is certified that error appears in the above-identified patent and that said Letters Patent is hereby corrected as shown below:

Column 3, line 19, change "end walls 23 and 27" to -- end walls 18 and 23 -- .

Column 5, line 25, change "surfaces" to -- surfaces 92 -- .

Column 7, line 52, change "end walls portions" to -- end walls -- .

Column 8, line 30, change "being position" to -- locking position -- .

Column 8, line 52, change "extended" to -- locking -- and "retracted" to -- releasing -- .

Column 8, line 56, change "recite din" to -- recited in -- .

Signed and Sealed this

Twenty-third Day of November, 1993

Attest:

BRUCE LEHMAN

Attesting Officer

Commissioner of Patents and Trademarks